US007063690B2

(12) United States Patent
Kessler et al.

(10) Patent No.: US 7,063,690 B2
(45) Date of Patent: Jun. 20, 2006

(54) ADAPTER FOR A PEG PROBE

(75) Inventors: Barbara Kessler, Kronberg (DE); Markus Schumacher, Aachen (DE); Barbara Breuer-Thal, Hattersheim (DE); Viktor Krütten, Birkheckerstr (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 450 days.

(21) Appl. No.: 10/431,034

(22) Filed: May 7, 2003

(65) Prior Publication Data

US 2003/0216712 A1 Nov. 20, 2003

Related U.S. Application Data

(63) Continuation of application No. PCT/EP01/12753, filed on Nov. 3, 2001.

(30) Foreign Application Priority Data

Nov. 8, 2000 (DE) ................................ 100 55 283

(51) Int. Cl.
*A61M 25/16* (2006.01)

(52) U.S. Cl. ....................................... 604/533; 604/910

(58) Field of Classification Search ........ 604/174–175, 604/264, 523, 537–539, 270, 910, 104; 606/108
See application file for complete search history.

(56) References Cited

U.S. PATENT DOCUMENTS 4,315,513 A * 2/1982 Nawash et al. ............. 604/537
4,393,873 A * 7/1983 Nawash et al. ............. 604/151
4,804,369 A * 2/1989 Lapeyre et al. ............. 604/175
5,197,634 A 3/1993 Beck .......................... 222/109
5,267,969 A * 12/1993 Hirsch et al. ............... 604/174
5,374,254 A * 12/1994 Buma .......................... 604/175
5,527,280 A * 6/1996 Goelz ...................... 604/99.02
5,549,657 A * 8/1996 Stern et al. ................. 604/537
5,836,924 A * 11/1998 Kelliher et al. ............. 604/248
6,019,746 A * 2/2000 Picha et al. ................. 604/175
2004/0193115 A1* 9/2004 Itrich et al. ................. 604/175

FOREIGN PATENT DOCUMENTS

| | | | |
|---|---|---|---|
| DE | 690 16 263 | T2 | 5/1990 |
| DE | 41 05 661 | A1 | 2/1991 |
| DE | 195 43 011 | A1 | 11/1995 |
| EP | 0 824 929 | A2 | 2/1998 |
| WO | WO 01/60292 | A1 | 8/2001 |

* cited by examiner

*Primary Examiner*—LoAn H. Thanh
(74) *Attorney, Agent, or Firm*—Heslin Rothenberg Farley & Mesiti P.C.

(57) ABSTRACT

An adapter is connected to a probe tube of a PEG probe that is already in place, the probe tube being cut off above the abdominal wall of the patient. The adapter comprises an outer retaining element, which is supported on the abdominal wall, and comprises structure for fastening the proximal end of the PEG probe, and structure for connecting a delivery line to the flow channel. A shut-off element having a rotatable or displaceable closing body is provided for closing the PEG probe. The adapter is characterized by its universal use, simple handleability and small overall height.

14 Claims, 3 Drawing Sheets

ADAPTER FOR A PEG PROBE

CROSS-REFERENCE TO RELATED APPLICATIONS

This application is a continuation of international application PCT/EP01/12753 filed Nov. 3, 2001, and published in German as WO 02/38102 A1 on May 16, 2002, and claims priority from German application 10055283.8 filed Nov. 8, 2000, which applications are incorporated hereby by reference in their entireties. This application is also related to commonly assigned, concurrently filed U.S. application Ser. No. 10/431,034.

BACKGROUND OF THE INVENTION

1. Field of the Invention

The invention relates to an adapter for subsequent shortening of a PEG probe which has already been put in place for artificial feeding.

2. Description of the Related Art

A PEG probe is fitted by introducing an endoscope or gastroscope into the patient's stomach and opening the stomach out by insufflation of air. A cannula is then advanced through the abdominal wall and stomach wall into the stomach lumen. A guide wire is introduced through the cannula into the stomach lumen, it is gripped with the endoscope or gastroscope and pulled back out through the patient's esophagus and mouth. With the aid of the guide wire which has been fitted in this way, the probe is then guided to the interior of the stomach and from there outward via the cannula. This procedure is also referred to as percutaneaus endoscopic gastrostomy (PEG).

At their distal end, the known PEG probes generally used have an inner retaining member with which the probe tube bears on the inner wall of the stomach. The probe tube is dimensioned so that it extends far out from the abdominal wall. At its proximal end the tube has a connection part in order to be able to connect the system for delivering nutrient solution. To close the probe tube, a conventional tube clamp or integrated closure cap is also often provided.

The known PEG probes have proven themselves in practice. However, a problem experienced by active patients is the fact that the probe tube protrudes relatively far out.

U.S. Pat. No. 5,549,657 describes a PEG probe which has an adapter for connection of a delivery system. The adapter is closed off by a Y-slotted valve which opens upon connection of the delivery system. To open the valve, the connection part of the delivery system has a protruding cannula which is inserted into the adapter. A disadvantage, however, is that the known PEG probe is not directly compatible with the conventional delivery systems which have a Luer lock connector. In addition, there is a risk that the slotted valve does not provide a complete seal and too quickly loses its ability to function.

U.S. Pat. No. 5,527,280 describes a probe for enteral nutrition which has a plurality of lumina. The probe has an adapter with a plurality of attachment pieces which can each be closed off with plugs.

DE 41 05 661 A1 discloses a device for long-term percutaneaus enteral nutrition. The flow channel of this probe too is closed off with a plug. No shut-off member with a rotatable or displaceable closure body is provided here either. DE 690 16 263 T2 describes a feed probe which again has an adapter that can be closed off with a plug.

U.S. Pat. No. 5,836,924 describes a PEG probe with a connection piece which is a component part of the probe tube. The connection piece of the PEG probe has a rotatable closure body for the flow channel.

SUMMARY OF THE INVENTION

The object of the invention is to make available a versatile, easy-to-use adapter which can be safely closed off and has a low structural height and with which it is possible to subsequently shorten the probe tube of an already fitted PEG probe.

The adapter according to the invention permits shortening of the probe tube of an already fitted PEG probe without the need to change the probe with the catheter tube still intact, the adapter being connected to the catheter tube cut off only a short distance above the abdominal wall.

To close the adapter, a shut-off member with a rotatable or displaceable closure body is provided. The shut-off member is of advantage because the delivery system does not need to have a special attachment part which opens the adapter upon connection. For this reason, it is in principle possible to attach all application systems for enteral nutrition (corresponding to EN 1615).

The outer retaining member of the adapter bearing on the abdominal wall should be made of a conformable elastic material, for example silicone rubber with especially good biocompatibility properties, while the other parts of the adapter should be made from shape stable materials, for example thermoplastics, in order to give the adapter the necessary stability.

The adapter is secured to the PEG probe preferably with two sleeve-shaped clamp parts which can be screwed to one another and clamp the proximal end of the fixed probe tube. The first sleeve-clamp part is expediently integral with the outer retaining member, although it can also be inserted loosely into the retaining member.

An elastic clamp ring is preferably fitted into the first clamp part, while a conical hollow stub is arranged concentrically in the second clamp part. Before screwing of the two clamp parts, the probe tube is guided through the first clamp part and pushed onto the hollow stub of the second clamp part. When the first clamp part and second clamp part are screwed together, the clamp ring exerts a radial pressing force on the tube, so that the latter is clamped on the hollow stub. In this way it is possible to obtain a sufficient tensile strength and compressive strength of the connection, without the tube being damaged at the clamp position.

In a preferred embodiment, the adapter, for the purpose of connection of the delivery tube, has a Luer lock connector which is distinguished by a low structural height and a very reliable connection.

The closure body of the shut-off member can be a cylinder body which is mounted so as to be able to rotate and which is closed off at one end and open at the other end and is provided with a transverse bore. When the closure body opens the shut-off member, fluid can flow out of the flow channel of the adapter through the transverse bore and into the cylinder body. This closure body makes it possible to arrange the Luer lock connector transversely with respect to the flow channel, by which means a particularly low structural height of the adapter is achieved and a lateral attachment of the delivery tube is possible.

However, the closure body can also be a valve piece which is pushed axially into the flow channel. This embodiment is of advantage if the Luer lock connector is to be arranged in the longitudinal direction of the flow channel, i.e. the delivery tube is not closed off laterally.

To simplify handling, the closure piece can be displaced by rotating the outer housing body of the adapter. The conversion of the rotation movement to a translation movement is preferably effected by means of a guide track.

Since the shut-off member closes the adapter tightly, it is in principle possible to dispense with an additional closure cap. However, the latter is of advantage as it protects the Luer lock connector of the adapter.

The retaining member is preferably designed as a plate-shaped body so that the adapter has the lowest possible structural height.

In an alternative embodiment, the securing means, the shut-off body and the connection means of the adapter form one unit which can be inserted with a tight fit into the retaining member. Different locking positions can be provided depending on the tube length. The fact that the retaining member does not get in the way during assembly makes it easier to secure the adapter on the probe tube.

An opening is provided in the retaining member for the passage of the probe tube. If the probe tube is guided through the opening of the retaining member and deflected through 90°, a particularly flat profile can be obtained. In this way, the retaining member can receive a short section of tube as reserve, so that the tube does not have to be cut off directly above the abdominal wall.

A guide for the tube is advantageously provided in the retaining member, which guide fixes the tube and reduces the risk of kinking at the bend point. However, the tube can also be fixed simply by the fact that the unit consisting of securing means, shut-off body and connection means sits with a positive fit in the retaining member.

BRIEF DESCRIPTION OF THE DRAWINGS

A number of illustrative embodiments of the invention are described in more detail below with reference to the drawings, in which.

DETAILED DESCRIPTION

Figure 1:
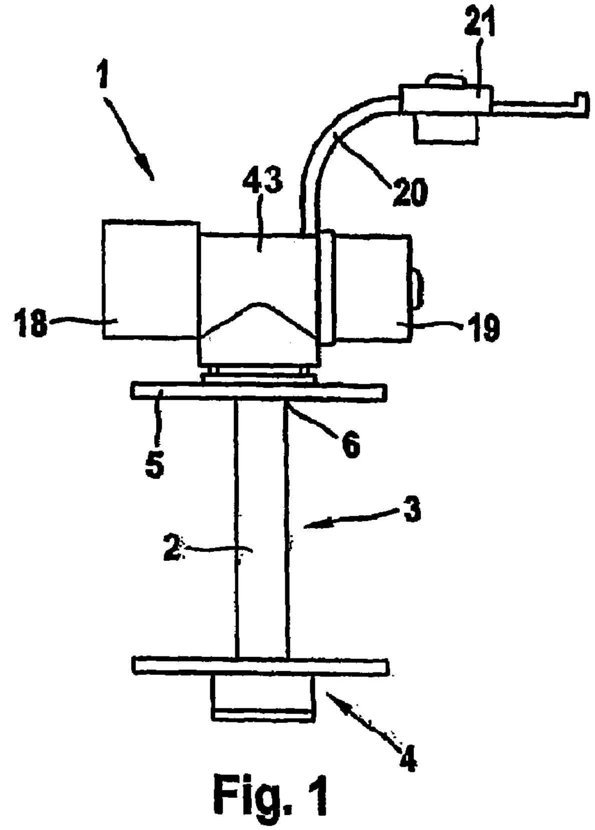
FIG. 1 shows a side view of a first embodiment of the adapter connected to a PEG probe.
Figure 2:
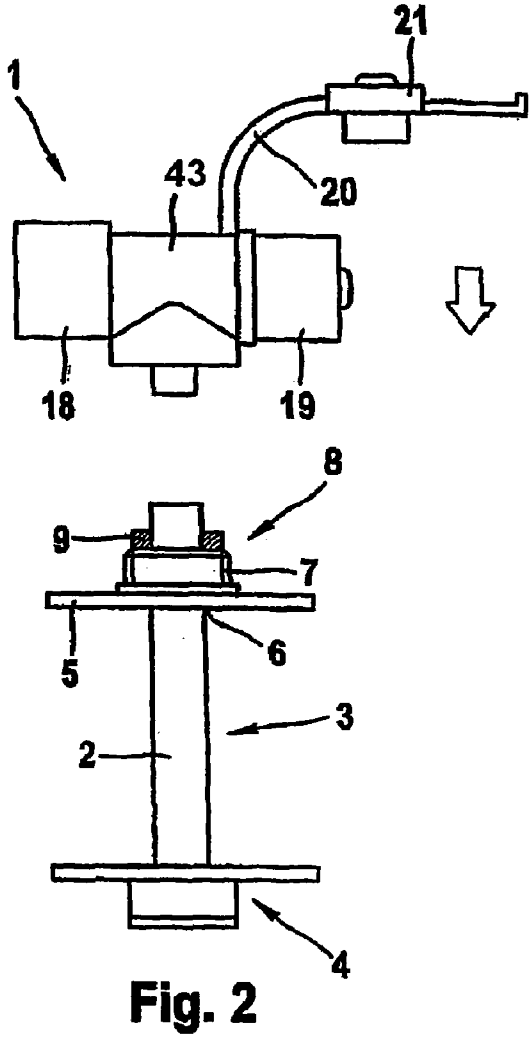
FIG. 2 shows the adapter from FIG. 1 removed from the PEG probe.
Figure 3:
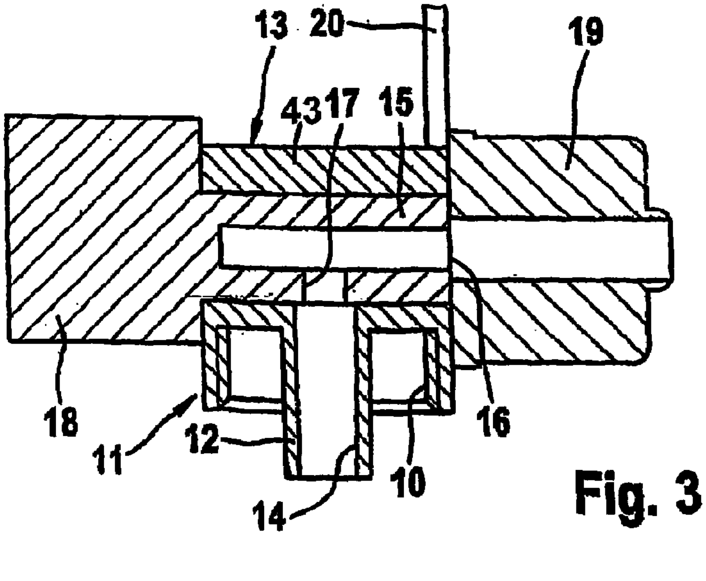
FIG. 3 shows the upper part of the adapter from FIG. 2 in cross section.

FIGS. 1 through 3 show a first embodiment of the adapter 1 for the probe tube 2 of a PEG probe 3. At its distal end, the probe tube 2 of the PEG probe 3 has a plate-shaped inner retaining member 4 with which the tube bears on the inner wall of the stomach. The outer retaining member 5, with which the PEG probe bears on the abdominal wall, is a component part of the adapter.

The retaining member 5 of the adapter is a circular plate made of a conformable, biocompatible material with a central opening 6 for passage of the probe tube 2. On the top face directed away from the patient, the retaining member 5 has a first sleeve-shaped clamp part 8 which is provided with an external thread 7 and into which an elastic clamp ring 9 is inserted through which the probe tube 2 is guided. A conical hollow stub 12 is arranged concentrically in a second sleeve-shaped clamp part 11 provided with a corresponding internal thread 10, and the probe tube 2 is pushed onto this hollow stub 12. To clamp the probe tube, the first and second clamp parts 8, 11 are screwed together, as a result of which the elastic clamp ring 9 exerts a radial clamping force on the tube.

Adjoining the second clamp part 11 is the housing body 43 of a shut-off member 13 in which a hollow cylindrical shut-off body 15 is rotatably mounted transverse to the longitudinal axis of the flow channel 14, which shut-off body 15 is open at one end 16, closed at the other end and provided with a central transverse bore 17. The cylinder shut-off body 15 can be turned by means of an adjusting screw 18 which is integral with the cylinder body. In front of the open end 16 of the cylinder body, a male Luer lock connector 19 is attached to the housing body 43. A flexible tab 20 is secured on the side of the housing body 43, on which tab 20 a closure cap 21 is arranged for closing the Luer lock connector 19.

To shorten the probe tube 2 of the already fitted PEG probe 3, the tube is cut straight above the abdominal wall, the protruding tube end is guided through the retaining member 5 with the first clamp piece 8 and is pushed onto the hollow stub 12 of the second clamp piece 11. The two clamp pieces are then screwed together.

The delivery tube (not shown) of the delivery system has a female Luer lock connector. To connect the delivery tube, the protective cap 21 is removed from the male Luer lock connector 19, and the two Luer lock connectors of adapter and tube are joined together.

Figure 4:
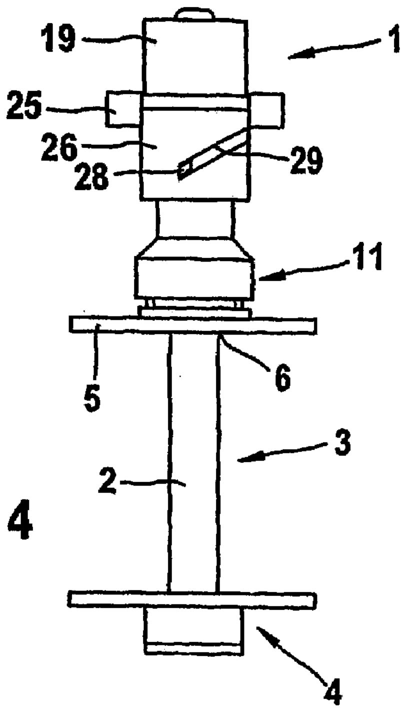
FIG. 4 shows a second illustrative embodiment of the adapter connected to the PEG probe.
Figure 5:
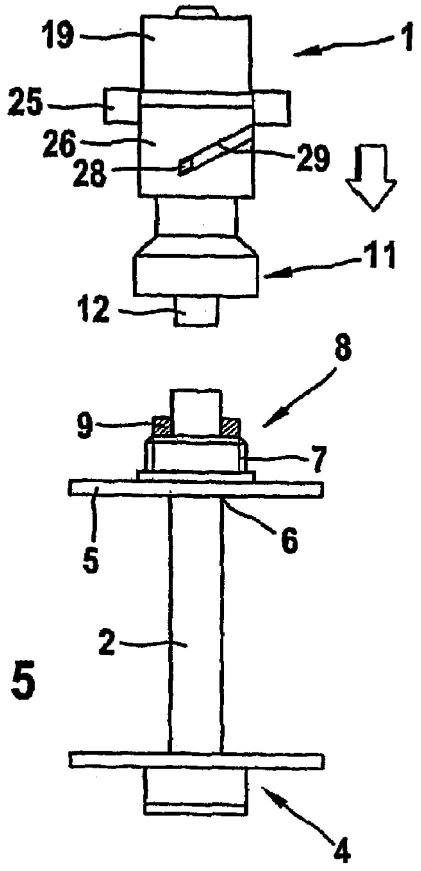
FIG. 5 shows the adapter from FIG. 4 removed from the PEG probe.
Figure 6:
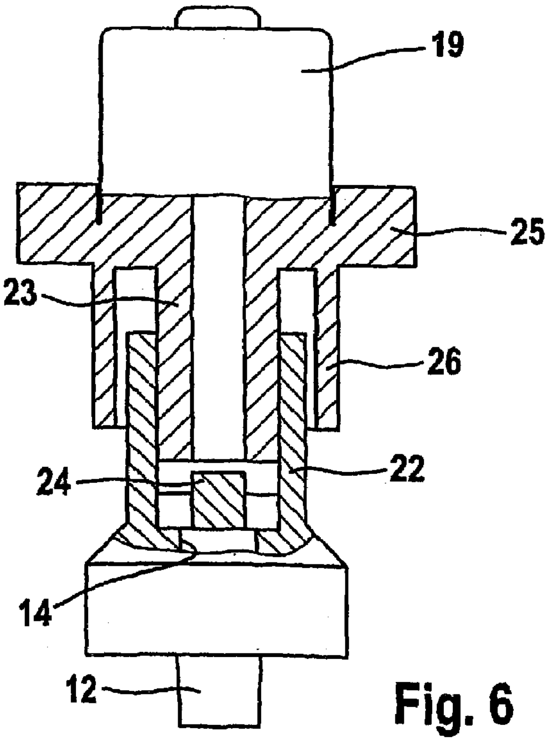
FIG. 6 shows the upper part of the adapter from FIG. 4 in partial cross section.

FIGS. 4 through 6 show a second illustrative embodiment of the adapter which differs from the embodiment according to FIGS. 1 through 3 in terms of the shut-off member. The parts of the illustrative embodiment according to FIGS. 4 through 6 which correspond to the parts of the embodiment according to FIGS. 1 through 3 are provided with the same reference numbers.

The adapter once again has a retaining member 5 with a first sleeve-shaped clamp part 8 and a second sleeve-shaped clamp part 11. An elastic clamp ring 9 is once again fitted into the first clamp part 8 so that, when the two clamp parts are screwed together, the probe tube 2 pushed onto the hollow stub 12 of the second clamp part is wedged fast.

In this embodiment, the second clamp part 11 merges into a lower hollow cylindrical body 22 in which an upper hollow cylindrical body 23 is guided in a longitudinally displaceable manner. A cylindrical closure piece 24 is arranged concentrically in the lower cylinder body 22. The male Luer lock connector 19 adjoins the open end of the upper cylinder body 23 in the longitudinal direction of the flow channel 14.

Provided on the underside of the Luer lock connector 19 is an annular attachment 25 from which there extends downward a sleeve-shaped body 26 which has a guide track 29 for a guide pin 28 extending radially outward from the lower cylinder body 22.

To close the PEG probe 3, the upper part of the adapter 1 is turned so that the upper and lower cylinder bodies 22, 23 are pushed together and the cylindrical closure piece 24 is guided sealingly into the lumen of the upper cylinder body.

The annular attachment 25 of the adapter can be provided with knurling or the like to permit better gripping of said adapter.

Figure 9:
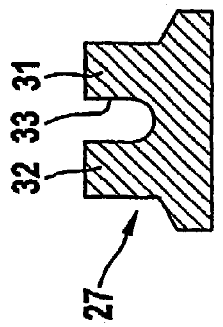
FIG. 9 shows a section through the retaining member of the adapter from FIG. 8 along line IX—IX.
Figure 7:
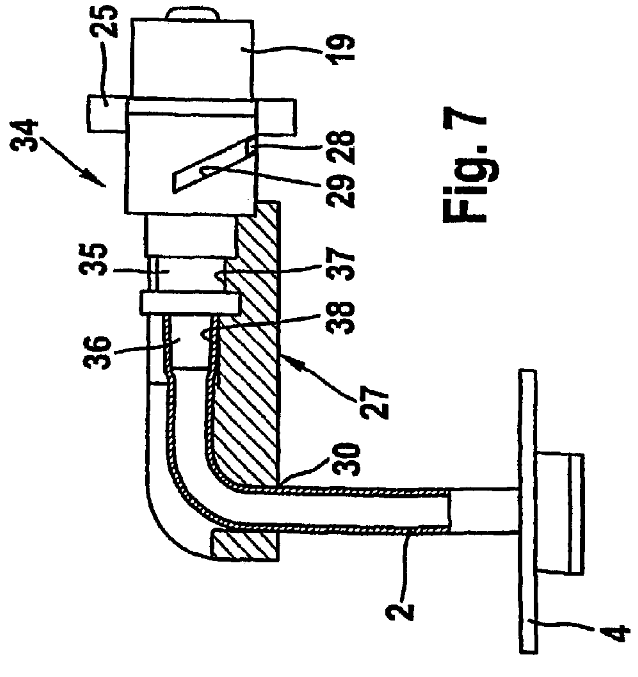
FIG. 7 shows a third embodiment of the adapter connected to the PEG probe in partial cross section.
Figure 8:
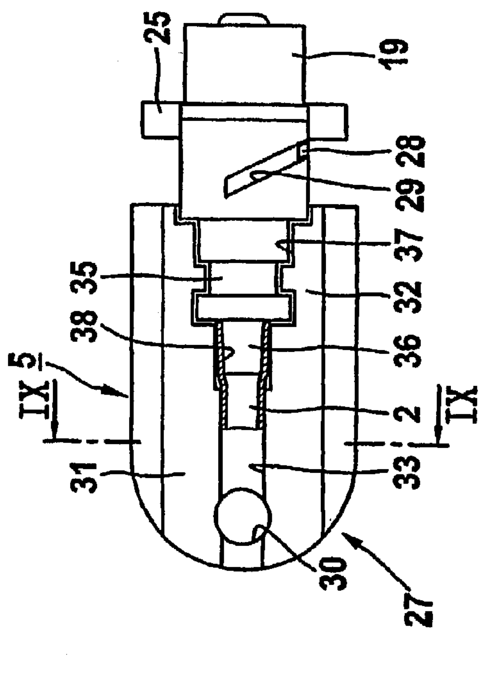
FIG. 8 shows a view of the adapter from the direction of arrow VIII in FIG. 7.

FIGS. 7 through 9 show a third embodiment of the adapter which differs from the illustrative embodiment according to FIGS. 4 through 6 in terms of the retaining member 5 and the means for securing the probe tube 2. The parts corresponding to one another are again provided with the same reference numbers.

The retaining member 27 is a plate-shaped element which bears with its flat underside on the abdominal wall. It has an opening 30 for passage of the probe tube. On its top face, two parallel webs 31, 32 delimit a guide channel 33 for the tube 2, said guide channel 33 adjoining the opening 30. In the embodiment according to FIGS. 7 through 9, the means for securing the probe tube, the shut-off member, and the means for connecting the delivery tube form one unit 34 which is inserted with a tight fit into the retaining member 27. The tube is secured on the adapter not by means of two clamp parts being screwed together, as in the illustrative embodiments according to FIGS. 1 through 6. Instead of the two clamp parts, the adapter according to FIGS. 7 through 9 has, at its end toward the tube, a profiled insert piece 35 with a conical hollow stub 36 onto which the tube is pushed. The insert piece 35 can be inserted into a correspondingly profiled recess 37 of the retaining member, which recess 37 adjoins the guide channel. The profiled recess 37 has a cylindrical portion 38 which receives and clamps the tube section pushed onto the hollow stub.

For connection of the adapter, the probe tube 2 is guided through the opening 30, cut to the correct length, and pushed onto the conical hollow stub 36 of the insert piece 35. The probe tube is then bent through 90° and fitted into the guide channel 33, and the adapter is fitted with the insert piece 35 into the recess of the retaining member. In the process, the tube section sitting on the hollow stub is fixed by being clamped. The guiding of the tube in the area of the deflection and in the area of attachment reduces the risk of kinking. The tube connection is otherwise unstressed, because the tube is fixed by being clamped. The positive connection between the insert piece of the adapter and the profiled recess of the retaining member affords further stability.

A plurality of locking positions can also be provided in the profiled recess for insertion of the insert piece, so as to be able to compensate for different lengths of the probe tube.

The areas of the retaining member 27 with direct skin and tissue contact consist of a conformable, biocompatible material, for example silicone rubber, whereas the other parts of the retaining member are made of a harder material, for example thermoplastics.

Figure 10:
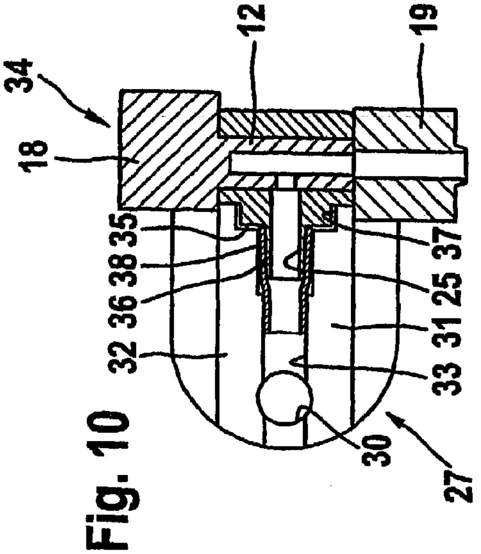
FIG. 10 shows a further embodiment of the adapter.

FIG. 10 shows a further illustrative embodiment of the adapter which differs from the embodiment according to FIGS. 7 through 9 in that use is made not of the shut-off member according to embodiments 4 through 6, but instead of the shut-off member according to FIGS. 1 through 3. Parts corresponding to one another are again provided with the same reference numbers.

The retaining member 27 again has an opening 30 for the probe tube 2 and a guide channel 33 which adjoins this opening 30 and into which the tube is fitted. The profiled insert piece 35 of the adapter with the conical hollow stub 36 is inserted with a tight fit into the correspondingly profiled recess 37 of the retaining member, the probe tube 2 being clamped in the cylindrical portion 38 of the recess of the hollow stub. The recess is designed in such a way that the adapter with the adjusting screw 18 and the Luer lock connector 19 bears on the side of the retaining member 27.

Figure 11:
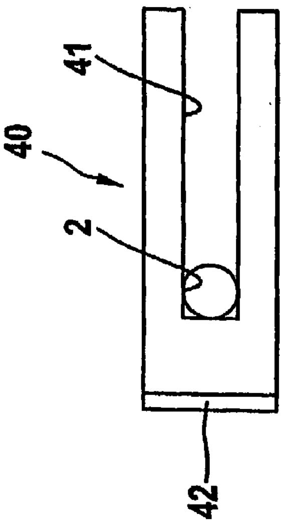
FIG. 11 shows a fixing element for the probe tube.

FIG. 11 shows a fixing element 40 ,for the probe tube 2 when fitting of the PEG probe. The fixing element is designed as a flat plate which is indented in the longitudinal direction. The indent 41 has a smaller width than the probe tube, so that the tube can be clamped with the fixing element. The thickness of the fixing element corresponds to the desired spacing between abdominal wall and outer retaining member 5 of the adapter. At the edge lying opposite the indent, the fixing element has a projecting attachment 42. To fit the PEG probe, the fixing element is placed on the abdominal wall and pushed laterally onto the probe tube until the limit stop 42 strikes against the retaining member, so that the tube is fixed by clamping. The probe tube is then cut off, and the retaining member is fixed on the probe tube. The fixing element here serves as a spacer.

What is claimed is:

1. A PEG probe adapter assembly comprising:

a PEG probe having an inner retaining member located at a distal end adaptable on an inner wall of a stomach and having an open proximal end, and an adapter having:

a flow channel, an outer retaining member adaptable on an abdominal wall of the stomach, means for securing the proximal end of the PEG probe on the outer retaining member, means for closing the flow channel, and means for connection of a delivery tube to the flow channel, wherein the means for closing the flow channel is a shut-off member which can be closed with a rotatable or displaceable closure body, and wherein the means for securing the PEG probe has a first sleeve-shaped clamp part, which is integral with the outer retaining member , and a second sleeve-shaped clamp part, said first and second clamp parts being screwed together so as to clamp the PEG probe.

2. The PEG probe assembly of claim 1, wherein the means for connection of the delivery tube is a Luer lock connector.

3. The PEG probe assembly of claim 2, wherein the Luer lock connector can be closed with a closure cap.

4. The PEG probe assembly of claim 3, wherein an elastic clamp ring is inserted into the first sleeve-shaped clamp part, and a conical hollow stub is arranged concentrically in the second sleeve-shaped clamp part.

5. The PEG probe assembly of claim 1, wherein the closure body is a cylinder body which is mounted so as to be able to rotate about an axis transverse to the flow channel and which is closed at one end and open at the an other end and is provided with a transverse bore, the means for securing the PEG probe being arranged at the open end of the closure body.

6. The PEG probe assembly of claim 1, wherein the closure body is a cylinder closure piece which can be pushed axially into the flow channel.

7. The PEG probe assembly of claim 6, wherein the cylindrical closure piece is arranged concentrically in a first cylinder body which is integral with the outer retaining member, and a second cylinder body, said first and second cylinder bodies being displaceable relative to one another by means of a guide.

8. The PEG probe assembly of claim 7, wherein a Luer lock connector is arranged on the second cylinder body in a longitudinal direction of the flow channel.

9. The PEG probe assembly of claim 1, wherein the outer retaining member comprises a plate-shaped body.

10. A PEG probe adapter assembly comprising a probe having an inner retaining member located at a distal end adaptable on an inner wall of a stomach and having an open proximal end, and an adapter having:

a flow channel, an outer retaining member adaptable on the abdominal wall, means for securing the proximal end of the PEG probe on the outer retaining member, means for closing the flow channel, and means for connection of a delivery tube to the flow channel, wherein the means for closing the flow channel is a shut-off member which can be closed with a rotatable or displaceable closure body, and wherein the outer retaining member has an opening, for passage of the PEG probe, and a recess, and wherein the means for securing the proximal end of the PEG probe, the shut-off member, and the means for connection of the delivery tube form one unit insertable into the recess.

11. The PEG probe assembly of claim 10, wherein the recess has a cylindrical clamp portion.

12. The PEG probe assembly of claim 11, wherein the outer retaining member has a guide channel which adjoins the opening.

13. The PEG probe assembly of claim 1, further comprising a fixing element for fixing a probe tube by clamping it, which fixing element comprises a small flat plate with a lateral indent.

14. The PEG probe assembly of claim 10, further comprising a fixing element for fixing a probe tube by clamping it, which fixing element comprises a small flat plate with a lateral indent.

* * * * *